United States Patent [19]
Gergely et al.

[11] Patent Number: 5,792,473
[45] Date of Patent: Aug. 11, 1998

[54] GRANULAR PRODUCT OR TABLET CONTAINING AN EFFERVESCENT SYSTEM AND AN ACTIVE PHARMACEUTICAL SUBSTANCE, AS WELL AS A METHOD FOR ITS PREPARATION

[75] Inventors: Gehard Gergely; Thomas Gergely; Irmgard Gergely; Stefan Gergely, all of Vienna, Austria

[73] Assignee: Gerhard Gergely, Vienna, Austria

[21] Appl. No.: 620,261

[22] Filed: Mar. 22, 1996

[51] Int. Cl.⁶ .................... A61K 9/46; A61K 9/16
[52] U.S. Cl. .................. 424/466; 424/489; 424/490
[58] Field of Search ......................... 424/466, 464, 424/465, 489, 490

[56] References Cited

U.S. PATENT DOCUMENTS

| | | | |
|---|---|---|---|
| 4,127,645 | 11/1978 | Witzel et al. | 424/44 |
| 4,704,269 | 11/1987 | Korab | 424/44 |
| 4,824,664 | 4/1989 | Tarral et al. | 424/43 |
| 4,867,942 | 9/1989 | Gergely et al. | 424/466 |
| 5,102,665 | 4/1992 | Schaeffer | 424/466 |
| 5,503,846 | 4/1996 | Wehling et al. | 424/466 |

FOREIGN PATENT DOCUMENTS

| | | |
|---|---|---|
| 1270781 | 1/1970 | European Pat. Off. . |
| 1274797 | 5/1972 | European Pat. Off. . |
| 0 076 340 | 8/1984 | European Pat. Off. . |
| 0 233 853 | 8/1987 | European Pat. Off. . |
| 0 396 335 | 11/1990 | European Pat. Off. . |
| 0 415 326 A1 | 3/1991 | European Pat. Off. . |
| 0019116 | 2/1976 | Japan . |
| 1505738 | 3/1978 | United Kingdom . |
| 2 142 820 | 1/1985 | United Kingdom . |
| WO 93/00886 | 1/1993 | WIPO . |

*Primary Examiner*—Gollamudi S. Kishore
*Attorney, Agent, or Firm*—Birch, Stewart, Kolasch & Birch, LLP

[57] ABSTRACT

In accordance with this invention there is provided a granular product with an effervescent system which comprises acid-sensitive pharmaceutically active substances, such as, for example, betacarotene, cimetidine, ranitidine or cisapride, which is specially useful to prevent antacid action, having an acid-neutralizing capacity below about 5 meq. at a weight of about 1.6 to about 2.3 grams. The effervescent grains are made from carrier crystals of at least one solid, edible organic acid, preferably citric acid and/or tartaric acid, and are present as a granular product, separate from the pharmaceutically active substance, and are coated with at least one layer of a neutral substance which is soluble in water and/or alcohol and which is able to bring about a melting point depression of the acid grains at their surface, such as, for example, a water-soluble polymer, a polyalcohol, a carbohydrate and/or a hydrocolloid. A second coating contains at least a part of the alkali and/or alkaline earth carbonate or bicarbonate provided for the total dosage.

71 Claims, No Drawings

GRANULAR PRODUCT OR TABLET CONTAINING AN EFFERVESCENT SYSTEM AND AN ACTIVE PHARMACEUTICAL SUBSTANCE, AS WELL AS A METHOD FOR ITS PREPARATION

CROSS-REFERENCE TO RELATED APPLICATIONS

This is a continuation-in-part application of PCT International application No. PCT/EP95/00650 filed on Feb. 23, 1995 which designated the United States, the entire contents of which are herein incorporated by reference.

FIELD OF THE INVENTION

This invention relates to a granular pharmaceutical preparation or more particularly a tablet containing an effervescent system and a—preferably acid-sensitive-pharmaceutical substance, such as cisapride, beta-carotene, an H2 blocker such as cimetidine or ranitidine, and/or a substance which is to be administered in an effervescent pharmaceutical preparation with comparatively small amounts of effervescent components or a comparatively low acid-neutralizing capacity.

BACKGROUND OF THE INVENTION

Heretofore it has been possible only with difficulty to incorporate acid-sensitive drugs in stable form into effervescent tablets or effervescent instant granular products, since in contact with the acid of the effervescent system such -compositions hydrolyze or decompose, i.e. they are not shelf-stable. Furthermore, whenever such a substance also affects the surface tension of water, frothing occurs which is highly undesirable for the consumption of the effervescent solution, or in any event, hydrophobic particles of the drug tend to creep upward on the glass. On the other hand, in certain cases, the antacid side-effect of an effervescent tablet is undesirable for many drugs.

Therefore an object of this invention is to provide an effervescent system which will avoid the aforesaid disadvantages and offer the possibility of administering to a patient pharmaceutical substances, inclusive of acid-sensitive substances which have hydrophobic properties or properties influencing the surface tension of water, in pleasant-to-drink effervescent solutions. It is a further object of this invention to create an effervescent tablet or an instant effervescent granular product with an acid neutralizing capacity of less than 5 meq. in order to avoid undesired antacid effects. This is especially advantageous for all H2 blockers. Lastly, it is desired that the tablet or granular product is to dissolve rapidly in water at a temperature of about 15°–20° C. in less than about 2 minutes.

SUMMARY OF THE INVENTION

The solution to the aforesaid problems can be achieved in a surprisingly simple, cost-effective and efficient manner in accordance with this invention e.g. by first substantially coating acid crystals with a composition comprising at least one neutral substance which causes a depression of the melting point of the acid crystals at their surface, and thereafter anchoring thereon at least one second coating which contains an alkali and/or alkaline earth carbonate and/or bicarbonate, and optionally a partial reaction product of the carbonate or bicarbonate with the same or a different organic acid.

The invention is more fully discussed in detail below along with a detailed discussion and illustration of several preferred embodiments.

DETAILED DESCRIPTION

Neutral substances soluble in water and/or alcohol (i.e. ethanol; mixture of ethanol/water) within the meaning of this invention include polymers soluble in water and/or alcohol, such as e.g. polyvinylpyrrolidone, and polyethyleneglycol of various chain lengths (e.g. 4,000–8,000). Carbopol (an acrylic acid polymer), polyvinyl alcohol, polyvinyl acetate, carbohydrates, such as saccharose, pentaerythritol, glucose, and fructose (although the latter two, under the influence of the only slightly alkaline effervescent-grain surface due to the bicarbonate coating, are subject to a Maillard reaction tending to make them yellow and therefore they are not particularly preferred herein), hydrophilic colloids, such as maltodextrin, dextrin, xanthan, guargum, tragacanth, galactomanan, carbopol, petkine and the like; especially preferred are polyalcohol, such as xylitol, mannitol and sorbitol. Suitable carbohydrates may be more specifically divided into three groups, including monosaccharides (i.e. dextrose, glucose and fructose), oligosaccharides (i.e. maltose, cellobiose, lactose and saccharose), and polysaccharides (i.e. dextrin, starch, cellulose and pektin).

Various embodiments of the invention are described in the defining clauses of the dependent claims.

It is true that WO93/00886 discloses that a foreign acid, possibly gluconic acid delta-lactone, which hydrolyzes to gluconic acid; can be incorporated at the surface of acid vehicle crystals, with the result that the crystal lattice is disturbed and a melting point depression is achieved. However, such a measure cannot of course provide adequate protection for acid-sensitive active substances. It has therefore also been impossible hitherto to use the invention of WO93/00886 for acid-sensitive active substances in practice.

It has also been proposed (British Patent 1,270,781) to coat acid vehicle crystals for effervescent tablets with a thin polymer layer, such as, for example, with polyvinylpyrrolidone, carboxymethylcellulose or the like. However, this results in an undesirable retardation of the dissolution time and, in the case of the 1 to 5% by weight of polyvinylpyrrolidone described there in the Examples, foam formation problems; furthermore, some acid is always transferred from the vehicle crystal to the layer in solution when the coating is applied by means of ethanolic or aqueous solution, whereby the acid-sensitive active substances would not be protected sufficiently. In addition, however, those skilled in the art have for over 20 years been unable satisfactorily to solve the problem of accommodating acid-sensitive active substances in effervescent systems not only in a shelf-stable manner but also in relatively small tablet weights with very low acid neutralizing capacity and short dissolution time. An effervescent tablet is generally defined as being particularly rapid when the dissolution (or complete suspending) of the tablet components takes less than 120 sec, preferably 90 sec or less.

According to the invention, however, after (preferably only a small amount of) the neutral substance has been coated onto the acid crystals, alkali and/or earth alkaline carbonate and/or bicarbonate particles are anchored on the crystal surface in order to prohibit an interaction between the acid and the active substance.

Furthermore, the process proposed in EP-A1-415 326 for coating acid vehicle crystals with several times the amount of sugar in order, in combination with bicarbonate, to achieve a slightly prickling effect, for a chewable tablet or lozenge has not been able to solve the combination of the problems or tasks: such a system would not be sufficiently reactive to dissolve an effervescent tablet in water within a reasonable time. It was the aim of the said EP-A1 to slow down the reaction between acid and carbonate in order not to produce an undesired high effervescent effect in the mouth.

If, as disclosed in the prior art (U.S. Pat. No. 4,127,645), a tablet having a core of acid, bicarbonate and calcium were coated with a neutral substance, for example with sorbitol in an aqueous, alcoholic or in a water/alcohol-solution, such a tablet would not provide reliable protection for acid-sensitive active substances contained in the core. However, if the mixture were pressed with a neutral substance (e.g. maltodextrin, if necessary as a mixture with sugar, U.S. Pat. No. 4,650,669; sorbitol with vitamins, U.S. Pat. No. 5,223,264, only suitable as a prickling chewable tablet) to give tablets, then either both reactants would be coated together or undesirable agglomerated granules would occur. In both cases, the reaction on dissolution of the tablet would take place too slowly and the dissolution time would thus be undesirably increased, or the solution would contain undesirably large amounts of sugar. Furthermore, it is very probable that, in agglomerated granules, acid crystals too would be present unprotected at the surface of the granules; however, this results in greater instability for acid-sensitive active substances.

In U.S. Pat. No. 4,867,942, a method is described in which vehicle crystals of a solid, edible organic acid are covered on their surface with a pre-reacted solution serving as buffer, particularly an acid alkali and/or alkaline earth salt of a solid, edible organic acid. Thereafter, more of the acid crystals and amounts of carbonate or bicarbonate are anchored side by side on this coating. Water which is released in the various neutralization partial reactions is removed by a final treatment with alcohol and vacuum drying. Such a process is disadvantageous, however, in that, for acid-sensitive drugs, on the acid crystal surface an additional acid simultaneously enters into a reaction with the alkali carbonate, and the reaction thus proceeds too fast and consequently not sufficiently uniformly. Therefore, the product that forms from this method cannot completely prevent the reaction of an acid-sensitive drug mixed in with it, due to the acid crystals lying on the surface of the granules.

In contrast, the structure of the effervescent system according to this invention not only prevents direct contact of an acid-sensitive drug with the acid crystals thereby providing an effervescent tablet or granular product with substantially more shelf-stability, but it also permits the preparation of substantially smaller tablets, i.e., those with smaller amounts of effervescent components which, when dissolved, result in a buffer system. Thus, the present tablets according to the invention, in contrast to buffer systems of antacid effervescent preparations, can remain at far less than 5 meq of acid neutralizing capacity (e.g. measured according to method 301 of United States Pharmacopeia (USPXXIII) Edition XXIII (1995)). Also, in terms of product preparation, a retarded reaction and better compressibility into tablets is obtained. With the aid of this invention, an effervescent tablet can be prepared which for the first time contains an acid-sensitive drug, such as cisapride, or an H2 blocker such as cimetidine, and which has an acid-neutralizing capacity of less than 5 meq for a tablet (or granular product) weight of only 1.6 to 2.5 g.

Further, in accordance with an especially advantageous embodiment of this invention, after the acid crystals have been covered with a coating of neutral substance, at least a portion of the carbonate and/or bicarbonate particles intended for a full dose can be applied to this coating, so that effervescent grains are formed from acid crystals on which a first coating of neutral substance has formed, and thereon a second coating of carbonate and/or bicarbonate, which has partially reacted with the acid in some cases.

The invention can be particularly expediently used for products or processes as described, for example, in EP-B1-76 340, U.S. Pat. No. 4,867,942 and WO93/00886, and whose description and claims are herein regarded as having been disclosed.

The application of the neutral substance, especially a sorbitol solution, for example, causes a depression of the melting point on the surface of the citric acid crystals. Thus, on the one hand, the adhesive force for the next coating containing alkali or alkaline earth carbonates and/or bicarbonates increases, and at the same time this signifies a slower and therefore more uniform reaction of the citric acid crystal surface and better passivation, so that the acid-sensitive drugs are less attacked by the effervescent grains. (Passivating means reducing the (acidic or alkaline) reactivity.) On the other hand, the melting point depression protracts the recrystallization time of the citric acid or of the citrates that have formed, which signifies better compressibility of the effervescent grains over a longer period of time.

The amount of neutral substance applied to the acid vehicle crystals depends on the amount of solvent with which the acid can be wet, since a maximum of 50–70% by weight can be dissolved in an aqueous solution. It is therefore preferably added in an amount of 0.05 to 1.0, in particular 0.07 to 0.8% by weight, based on the acid. Additions of less than 0.07 have only a weak effect and those of less than 0.05 have no effect which is relevant according to the invention: the shelf-stability of acid-sensitive active substances is reduced. Additions of over 0.8 generally begin to have an interfering effect, and at above 1.0 the reactivity of citric acid crystals and of the effervescent system is considerably slowed down.

However, this may be less troublesome in the case of grains since a longer dissolution time tends to be desirable there in order to allow the crystals to sink on introduction into water and only thereafter to undergo a reaction for dissolution. Otherwise, however, the amounts of neutral substance which can be applied to, for example, citric acid crystals are determined by the amount of solution with which the citric acid can be wet, since the neutral substances are in fact applied in solution, and a 50 to max. 70% solution can be prepared. The citric acid crystals cannot be wet with an infinitely large amount of water and hence solvent.

In certain circumstances, the neutral coating, especially if carbonate and/or bicarbonate particles are anchored on it, can also contain small amounts of a solid, edible organic acid, and in some cases an acid different from the one of which the vehicle crystals consist—as disclosed per se in another context—but here also in order to intensify the melting point depression and/or to control the effervescent reaction and rate of dissolution.

Each such effervescent grain is, taken by itself, actually a small effervescent "tablet", and effervesces by itself. Therefore, if desired, a short disintegration time, small quantity and low acid-neutralizing capacity can be achieved.

Experiments thus far towards achieving a fast-acting, small effervescent tablet by the use of monosodium citrate instead of citric acid crystals have failed, because this greatly slows the effervescent reaction, since the monosodium citrate reacts more slowly with sodium bicarbonate, and such tablets usually have an acid consuming capacity exceeding 5 meq.

On the other hand, a very thin monosodium citrate coating in accordance with this invention, especially as a third or fourth layer, which can contain an additional neutral substance if desired, acts advantageously because 1 mol of monosodium citrate binds 1 mol of water of crystallization and thus contributes to the drying or to maintenance of dryness. Furthermore, in any case, uncovered citric acid crystals surfaces can be covered again or more completely with bicarbonate.

Additionally, since many substances exhibit some form of taste sensation of which many are unpleasant, especially those exhibiting bitterness, it is desirable to keep the final effervescent solution, especially since it is in beverage form, within the pH range of 3.8 to 4.6. Experience has shown that within this range particularly bitter substances can be more effectively masked.

While not obligatory, it is preferable to remove residual water from the reaction granules in the course of their preparation by a final treatment with alcohol. Alcohol may disrupt the bonding of water of crystallization, because during drying the residual moisture is removed along with the alcohol by evaporation. Small amounts of an antifoaming agent can also be added to the alcohol in order to accelerate the dissolution of the final tablet.

Many of the aforementioned drugs, especially cimetidine and cisapride, often cause frothing in an effervescent tablet. This is not due, however, to foaming such as that caused by tensides. That is to say, the active agents themselves, when stirred into water, do not foam. Instead, when the effervescent grains in the tablet dissolve, bubbles of carbon dioxide form.

These bubbles burst and leave the $CO_2$ on the surface. Now, if a less soluble or more hydrophobic substance is present, the undissolved particles envelop the $CO_2$ bubbles, and by forming such a film successfully prevent rapid bubble bursting, so that the bubbles with this film on the surface collect and thus a "foam" is formed. However, the "foam" already forming between the effervescent grains interferes with the continued reaction, and thus with the rapid dissolution of the tablet or granules. This circumstance is combatted according to the invention by the addition of very small amounts of at least one antifoaming agent with the result that any "foam" that forms as the effervescent reaction begins immediately collapses.

The antifoaming agent is preferably added in an amount of 0.005 bis 0.5% by weight, based on the total amount including any fillers, flavors, etc., or 0.05-2.0% by weight, based on active substance. Additions of less than 0.005 have no effect relevant according to the invention; additions of more than 0.5 give rise to troublesome or unacceptable side effects.

In the case of active substances which are soluble, although not too freely soluble, as in the case of cimitidine, a percentage of simethicone of 0.1-0.3% by weight, based on active substance, is used, which is equivalent to the use of 0.016-0.028 percent (about 0.03%) based on the total tablet weight. The situation is somewhat different in the case of an insoluble hydrophobic active substance, such as cisapride (the monohydrate is used), where 1% of simethicone is used, based on the active substance, but an amount of 0.006% results when based on the tablet weight of 1.6 g. It is evident that the cisapride, as a slightly soluble, hydrophobic active substance, requires a larger amount of antifoaming agent for suppressing the foam, but the required fillers and the effervescent base result in a substantially smaller amount of simethicone being used per tablet, so that the ratios are inverted.

In the case of the soluble active substances, such as cimetidine and ranitidine, the simethicone is required in smaller amounts, in order to suppress the smaller tendency to foaming in the local reaction on dissolution of the effervescent tablet, whereas in the case of cisapride—as already mentioned—the tendency to foam is substantially greater and the principle is therefore also slightly different.

If larger amounts are used, film formation of simethicone occurs at the surface after dissolution of the effervescent tablet, by virtue of the fact that—especially in the case of insoluble active substances—particles of the active substance collect and remain hanging and thus result in unattractive dissolution behavior, this film then additionally having the tendency to form a ring on the glass wall.

In some cases, however, very small amounts of a tenside, for example, docusate sodium, are also added. Due to their wettable nature, such drug particles dissolve more quickly and no longer adhere to the foam bubbles. The proportion of such substances must be determined very precisely to achieve the desired dissolving characteristics.

Although in some cases the antifoaming agent can be applied to the effervescent system and/or to the drug, this is not preferred according to the invention. In the first case, it might cause undesirable slowing of the dissolution and reaction of the effervescent components unless very slight amounts of antifoaming agent sufficient for the achievement of the desired effect are used. In the second case, only those drugs are involved which, when the antifoaming agent is drawn onto them from a solution in a solvent (e.g., methyl ethyl ketone and acetone) at 40° C., do not lose any of their solubility or stability. Additionally, in the course of production with the use of finely powdered drugs the addition of antifoaming agents may lead to poor distribution because of drug particles attaching themselves to the antifoaming agent droplets.

It is therefore preferred, in accordance with this invention, that first the formation of a typical granular product from antifoaming agents and a neutral substance is undertaken, which product is thereafter mixed with the effervescent system and the drug, plus additional adjuvants if desired (e.g., flavors, sweeteners and the like) and the mixture then compressed into tablet form.

The moisture released in the preparation of the effervescent system by the neutralization reaction, and not entirely removed by heating and/or vacuum treatment, as well as moisture picked up from the air during storage, can best be bound by the addition of a moisture-binding agent, especially anhydrous sodium carbonate (which can absorb 10 mols of water per mol) or sodium sulfate. The agent can be bound either by applying it to one or more of the coatings applied to the vehicle crystals, or by adding it to the total mixture. This improves shelf life because the reaction of the acid-sensitive active agent with the acid is further suppressed or completely prevented by the reduction of moisture. However, excessive amounts of such moisture-binding agent, for example sodium carbonate, are not desirable as it may retard the effervescent reaction.

Sodium carbonate as a drying agent, therefore, should not be used for completely covering the effervescent grains, since it is preferable to operate with only small quantities effective to merely dry the residual moisture, or to retard the reaction during manufacture, and to avoid undesirably lengthening the disintegration time of the tablet. Therefore, the final addition of sodium carbonate should not be used for complete coverage (or a tablet-coating), due to both the quantity and the grain size (approx. 0.1–0.05 mm), and it is therefore not suitable for producing a continuous coating on the bicarbonate already present. However, it can be partially hooked onto the effervescent grains. It is also possible, however, not to add the sodium carbonate until after the drying operation.

In principle, the percentage amount of sodium carbonate per tablet depends on several factors, such as, for example, the amount of effervescent base used, the amount and type of the fillers used, the presence of other carbonates, such as, for example, calcium carbonate, etc.

The moisture-binding agent, in particular sodium carbonate, is preferably added in an amount of between 1 and 10, in particular 4–6,% by weight (based on the total amount, including any fillers, flavors, etc.). Additions of less than 4 have only a weak effect, and with those of less than 1, the drying effect and increase in stability is too small, they have no effect relevant according to the invention. Additions of over 6 generally begin to have a troublesome effect because sodium carbonate dissolves more slowly and reacts more poorly; above 10% the dissolution time is already significantly lengthened, since sodium carbonate first absorbs water (up to 10 molecules of water of crystallization) on dissolution of the effervescent tablet, i.e. is calcined and only then reacted with the citric acid crystals.

Here it is to be emphasized that 1 mol of water of crystallization can be bound per mol by trisodium citrate alone incorporated in or on the sorbitol layer, and in spite of any residual moisture present the sorbitol layer prevents or hinders any acid harm to the drug.

If all of the prescribed steps are followed in accordance with the invention, effervescent tablets can be produced, even with the difficult substances referred to, which at a tablet weight of, e.g., 1.6 g, will attain a disintegration time of less than 100 seconds. It is also to be noted that especially cimetidine, due to its hydrophobic character, further lengthens the disintegration time in comparison with other drugs, under otherwise equal conditions.

Granulation with sorbitol solution permits rapid dissolution without the incorporation of an extraneous acid that is otherwise necessary, for example, according to WO93/00886.

Furthermore, during the preparation of the effervescent systems of this invention, and in any case of the tablets themselves, the steps taken according to the invention will enable the control of reactions which take place at the surface of individual crystals or granules, which thus constitutes a local mechanism, while also during dissolution the above-described desired advantages will be achieved throughout.

The system is also extraordinarily well suited for the processing of substances which are both acid-sensitive and sparingly soluble in water. Such substances, such as cisapride for example, exhibit very unpleasant behavior in suspension, since, as mentioned above, they tend to froth together with the effervescent system, adhere to a glass wall, form unpleasant rings and tend to agglomerate on the surface of the drink.

All the aforesaid problems can be effectively combatted by preparing separate granules. For this purpose in yet another embodiment of this invention, there is provided a vehicle which can consist of an Aerosil and/or a neutral substance, on which the drug is applied preferably with the surface of its particles partially dissolved, and/or with binding agents and/or tensides if desired, and dried, or is bound to the vehicle surface by means of binders.

Thus, the tablet or granular product according to the invention may comprise at least one hydrophobic pharmaceutically active substance present in particles separate from said effervescent grains, in which particles of said at least one hydrophobic substance is anchored on or coated onto at least one substance selected from the group consisting of a said neutral substance such as mannitol or sorbitol, and a suspending agent such as Aerosil (i.e. microdispersed silica) or Avicel (i.e. microcrystalline cellulose).

The amount of the suspended substance is limited to at most 8, preferably at most 4.5,% by weight (based on the total mixture), for example for cisapride, since larger amounts would result in increased sinking of the granule particles after dissolution of the tablet. On the other hand, the amount of binder used is likewise limited to 1% by weight, since it otherwise leads to undesirable agglomerated granules of active substance, suspended substance and binder, which dissolve only with difficulty and then sink to the bottom, i.e. prevent the desired suspension.

Alternatively, the drug can also be dissolved in the methyl ethyl ketone or in acetone and coated onto mannitol, Aerosil® and sodium bicarbonate.

The invention will now be more fully described and understood with reference to the following examples of preferred embodiments. It is to be understood, however, that these examples are for illustrative purposes only, and many other embodiments and variations will be readily apparent to those persons skilled in the relevant art and are not intended to limit the scope of this invention or the claims or the spirit thereof in any way.

EXAMPLE 1

Preparation of effervescent tablets containing 200 mg of cimetidine:

a) Preparation of the effervescent system 102 parts by weight of coarse citric acid and 25 parts by weight of finely powdered citric acid (the latter is preferable for improving build-up to effervescent grains on the vehicle crystal as the powder particles provide a rough surface on which up to about 30% of bicarbonate can be anchored) or tartaric acid are aspirated into a preheated vacuum tank and heated to approx. 60° C. with stirring. Next, 0.85 parts by weight of a solution 1, which has been formed from 36 parts by weight each of water and sorbitol, 21 parts by weight of citric acid and 7 parts by weight of sodium bicarbonate particles, is aspirated and distributed on the citric acid by mixing. Thereafter, 52.5 parts by weight of sodium bicarbonate and 4.4 parts by weight of aspartame are added to this mixture, which is then stirred and dried by a vacuum of up to 200 mbar, after which 1.9 parts by weight of sodium carbonate are aspirated and distributed in the mixture by stirring, and the mixture is then dried by a vacuum of up to 15 mbar.

Next, a further 0.6 parts by weight of said solution are aspirated and distributed in the mixture by mixing. The resultant effervescent grains are dried in a vacuum of up to 20 mbar with stirring. If necessary, 0.25 parts by weight of 96% ethanol are also employed to dry the mixture, and aspirated. Then, again 9.3 parts by weight of sodium carbonate are bound onto the effervescent grain surface. After another final drying, the product is removed through a sieve.

b) Preparation of the granulated antifoaming agent:

In a vacuum mixing tank with a jacket temperature of 80° C., 7.7 parts by weight of sorbitol powder are added and heated to 50° C. Then, 0.2 parts by weight of simethicone in a 30% butanone/acetone mixture (5:3) are aspirated in, stirred by vibrational mixing and dried under full vacuum down to 15 mbar at a temperature of at least 45° C.

c) Preparation of the total mixture

In a mixer, 20 parts by weight of cimetidine, with 21.1 parts by weight of sorbitol powder if desired, are mixed for 10 minutes at 6 rpm with 178.4 parts by weight of the effervescent system prepared in a). Then 7 parts by weight of the antifoaming agent particles prepared in b) and screened through a 0.6 mm sieve, and 4.5 parts by weight of lemon flavoring, are added, mixed for another 5 minutes at 6 rpm. The final mixture is pressed into tablets which weigh 2.3 g, contain 200 mg of cimetidine, and have a hardness of 6–8 kp.

EXAMPLE 2

Preparation of effervescent tablets containing 200 mg of cimetidine, and citric and malic acid in the effervescent grains:

102 parts by weight of coarse citric acid, 25 parts by weight of powdered citric acid and 1.1 parts by weight of malic acid are heated to 60° C. with stirring in a preheated vacuum tank. A solution consisting of 0.4 parts by weight of water, 0.22 parts by weight of sorbitol and 0.22 parts by weight of malic acid is then aspirated in and distributed onto the citric acid by mixing. 52.5 parts by weight of sodium bicarbonate and 4.4 parts by weight of aspartame are next added to the mixture and dried by stirring, in a vacuum of up to 200 mbar. Next, 1.9 parts by weight of sodium carbonate are aspirated in and distributed in the mixture by stirring, and then vacuum drying is performed down to 15 mbar. Finally, a final drying can be performed with ethanol, and then 9.3 parts by weight of sodium carbonate are added to the mixture. The rest of the procedure is similar to Example 1.

EXAMPLE 3

Effervescent tablets containing 400 mg of cimetidine, and mannitol as a neutral substance:

49 parts by weight of citric acid are aspirated into a preheated vacuum tank and heated with stirring to 60° C. Then, 0.45 parts by weight of a solution 1, which has been prepared from 0.25 parts by weight of water and 0.20 parts by weight of mannitol, is aspirated in and distributed on the citric acid by mixing, whereupon 14.7 parts by weight of sodium bicarbonate and 3.2 parts by weight of aspartame are then added. Reaction is started with stirring and then drying is performed with a vacuum up to 200 mbar. 0.5 parts by weight of sodium carbonate are next aspirated and distributed in the mixture by stirring, and then drying is performed with a vacuum to 15 mbar. Then 0.5 parts by weight of a solution 2, which has been prepared from solution 1 by the addition of 0.16 parts by weight of monosodium citrate, is aspirated into the mixture and distributed by mixing. The effervescent grains obtained therefrom are then dried by vacuum and stirring to 20 mbar, and finally 2.8 parts by weight of sodium carbonate are added. To this mixture is then added 17.3 parts by weight of cimetidine, 4.3 parts by weight of mannitol, 8 parts by weight of sorbitol, 0.9 parts by weight of flavoring, and 4 parts by weight of antifoaming agent particles prepared according to Example 1 b), until distribution is uniform.

EXAMPLE 4

Effervescent tablets containing 300 mg of cimetidine, as well as maltodextrin as a neutral substance:

Similarly to Example 3, for a 300 mg cimetidine effervescent tablet, a 50% solution of maltodextrin is selected, which is then used in the same amount as in the case of the 400 milligram form.

In all of the examples in which the tablets contain 100 to 400 mg of cimetidine, the tablet weight can be 2.3 g. The tablets have a disintegration time of preferably 60 to 150 seconds and a buffering capacity below 5 meq. measured according to test 301 of USP XXIII (acid-neutralizing capacity), by back-titration (with 0.5 mol/l NaOH) of an effervescent tablet dissolved in 70 ml of water and with 30 ml of 1.0 mol/l HCl added.

The figures given in the following table 1 are the percentages of individual ingredients in the particular total mixture of the illustrated preferred embodiments, which therefore are in the following preferred ranges:

TABLE 1

| Cimetidine | 2–30% | (corresponds to an effervescent tablet containing 50 to 600 mg of cimetidine) |
|---|---|---|
| Citric acid | 30–60% | sorbitol 5–20% |
| Sodium bicarbonate | 10–30% | mannitol 2–10% |
| Sodium carbonate | 2–10% | simethicone 0.005–0.5% |
| Aspartame | 1–4% | flavoring 0.1–3% |

A preferred percentage composition of cimetidine effervescent tablets or bags of granules containing 100, 200, 300 and 400 mg of cimetidine, with a total weight of 2.31 grams, is summarized below in table 2:

TABLE 2

|  | 100 mg | 200 mg | 300 mg | 400 mg |
|---|---|---|---|---|
| Cimetidine | 4.30 | 8.70 | 13 | 17.3 |
| Citric acid | 50 | 50 | 48.2 | 48.2 |
| Trisodium citrate | 0.04 | 0.04 | 0.04 | 0.04 |
| Aspartame | 1.74 | 1.64 | 2.54 | 3.24 |
| Sorbitol | 12.5 | 12.5 | 12.8 | 8.00 |
| Sodium bicarbonate | 20.7 | 20.7 | 14.7 | 14.7 |
| Sodium carbonate | 4.4 | 4.4 | 3.5 | 3.3 |
| Mannitol | 4.3 |  | 4.3 | 4.3 |
| HMA Lemon flavoring | 2.0 | 2.0 | 0.9 | 0.9 |
| Simethicone | 0.02 | 0.02 | 0.02 | 0.02 |

EXAMPLE 5

Cisapride effervescent tablets a) Preparation of the effervescent grains:

655 parts by weight of crystalline citric acid, 70 parts by weight of citric acid powder and 8 parts by weight of saccharin sodium are heated while mixing to 60° C. Then 2.8 parts by weight of a solution consisting of 0.6 parts by weight of sorbitol, 0.3 parts by weight of trisodium citrate, 0.5 parts by weight of citric acid and 1.6 parts by weight of water are aspirated into this mixture and distributed by mixing. Next, 340 parts by weight of sodium bicarbonate as well as 2 parts by weight of aspartame are added and reacted. Before drying, 77 parts by weight of sodium carbonate are added, whereupon the mixture is vacuum dried with slow stirring to 15 mbar.

b) Preparation of the granulated drug:

Insoluble and hydrophobic cisapride is attached to a suspending substance by means of a binder and a small amount of a tenside as follows: A solution of 10 parts by weight of cisapride, 2 parts by weight of polyvinylpyrrolidone and 0.8 part by weight of docusate sodium in 1 part by weight of ethanol and 40 parts by weight of acetone is applied to 10 parts by weight of Aerosil®, uniformly distributed and then dried while stirring. The particles are sieved to 0.1–0.3 mm.

c) Preparation of the final mixture:

To 1152 parts by weight of effervescent grains are added 50 parts by weight of maltodextrin, 100 parts by weight of lactose, 184 parts by weight of mannitol, 40 parts by weight of flavoring, 50.2 parts by weight of anti-foaming particles (0.2 parts by weight of simethicone dated onto 50 parts by weight of mannitol), as well as the granulated drug prepared in b), mixing is carried out for 15 minutes for uniform distribution and the mixture is then pressed to form tablets of 1.6 g, which have an acid-neutralizing capacity of only 2 meq. Cisapride effervescent tablets having such a low acid-neutralizing capacity are unknown to date.

EXAMPLE 6
Beta-carotene effervescent tablets

With this extremely acid- and oxidation-sensitive substance, attention must be paid to an especially good covering of the acid. The surface and the contact zone on the beta-carotene must be kept alkaline. Therefore the effervescent grains are covered at least in part with calcium carbonate, thus insuring an alkaline surface. This, however, does result in a slightly longer disintegration time, which in this case is desirable, because the beta-carotene needs time to suspend while the tablet is disintegrating. Large amounts of sorbitol, as in U.S. Pat. No. 5,223,264 mentioned at the outset, are by no means suitable for a beta-carotene effervescent tablet which is intended to be dissolved or suspended in water.

a) Preparation of the effervescent grains:

1315 parts by weight of citric acid, 7 parts by weight of sodium saccharin and 45 parts by weight of sodium cyclamate are heated in a vacuum tank to 50° C. Then 16.8 parts by weight of a solution prepared from 3.6 parts by weight of calcium carbonate, 19 parts by weight of citric acid, 12 parts by weight of sorbitol, and 45 parts by weight of water are sucked in and distributed onto the citric acid by mixing. Next, 400 parts by weight of calcium carbonate and 190 parts by weight of citric acid are added and the mixture heated with stirring to 60° C. Then follows the second granulation with 44 parts by weight of the above-mentioned solution, and after distributing and mixing, 403 parts by weight of sodium bicarbonate are added, and also, before drying, 52 parts by weight of sodium carbonate. The mixture is then vacuum-dried to 15 mbar with slow mixing.

b) Preparation of the final mixture:

130 parts by weight of sorbitol and 540 parts by weight of mannitol and 50 parts by weight of flavoring, an encapsulated beta-carotene suspendable in water and corresponding to 2 to 15 parts by weight of 100% beta-carotene [i.e. pure beta-carotene; usually available in the form of adsorbates with 10–25% of the pure substance], plus, if desired, 50 to 250 parts by weight of vitamin C and/or an amount of a solid tocopherol acetate suspendable in water corresponding to 10 to 75 parts by weight of 100% tocopherol acetate [i.e. pure tocopherol acetate; usually available in the form of adsorbates and/or dry mix powders with only 50% or 25% of the pure substance], plus still other vitamins if desired, are mixed with 2415 parts by weight of the effervescent grains prepared according to a). The product has a tablet weight of 3.3 g and its disintegration time is 60 to 90 seconds.

EXAMPLE 7
Ranitidine effervescent tablets a) Preparation of the effervescent grains:

840 parts by weight of crystalline citric acid, 210 parts by weight of citric acid powder, 45 parts by weight of sodium cyclamate, and 4 parts by weight of sodium saccharin are heated in a vacuum mixing tank at 60° C. Then a solution consisting of 6 parts by weight of water, 1 part by weight of trisodium citrate, and 3 parts by weight of sorbitol is aspirated in and distributed by stirring. 500 parts by weight of sodium bicarbonate are next added and allowed to react, and thereafter 370 parts by weight of monosodium citrate are added, which are also allowed to react. Lastly, 100 parts by weight of sodium carbonate are added and the granules are dried with slow stirring up to 15 mbar.

b) Preparation of the final mixture:

To the effervescent grains thus prepared, 167 parts by weight of ranitidine hydrochloride, 125 parts by weight of mannitol plus 100.4 parts by weight of a granulated anti-foaming agent (consisting of 100 parts by weight of mannitol and 0.4 parts by weight of simethicone) and the flavoring agent are added. This mixture is mixed for 15 minutes for uniform distribution, and then pressed to tablets of 2.5 g. The tablets have a disintegration time of 60 to 80 seconds and an acid-neutralizing capacity of about 2 meq and contain (in percent by weight) 6.8 ranitidine hydrochloride, 42.0 citric acid, 14.8 monosodium citrate, 20.0 sodium bicarbonate, 4.0 sodium carbonate, 2.0 sweeteners, 5.0 mannitol, 0.1 sorbitol, 4.0 granulated anti-foaming agent (containing 0.016 dimethylpolysiloxane) and 1.2 flavoring.

EXAMPLE 8

545 parts by weight of crystalline citric acid and 133 parts by weight of powdered citric or tartaric acid are mixed while heating to 60° C. Then, as the first coating, a solution-which consists of 6 parts by weight of water and 4 parts by weight of sorbitol is distributed on the surface by stirring. Next, 222 parts by weight of sodium bicarbonate are made to react on the surface of the citric acid, and finally 80 parts by weight of sodium carbonate are added. The product is dried with slow stirring. The particles are screened to 1.5 mm, and then mixed for 10 minutes at 10 rpm with 167 parts by weight of ranitidine hydrochloride, 100 parts by weight of anti-foaming particles (containing 0.4 parts by weight of simethicone and 100 parts by weight of lactose), plus 54 parts by weight of sweetener-and 40 parts by weight of flavoring, until uniform distribution is obtained. The mixture is then pressed to tablets weighing 1.43 g and having a disintegration time of 65–70 sec, a hardness of 8, and an acid-neutralizing capacity of about 1.5 meq. The product contains no monosodium citrate. Ranitidine effervescent tablets having such a low acid-neutralizing capacity have not been disclosed to date.

EXAMPLE 9

38.2% of citric acid is heated with 0.26% of sodium saccharin to 60° C., then two-thirds of a solution which consists of, with respect to the final mixture, 0.6% water, 0.18% sorbitol, and 0.12% trisodium citrate is applied. The solution is distributed for 5 minutes by mixing at 10 rpm. Then 16.2% of sodium bicarbonate and 2.9% of aspartame are added and anchored on the surface of the citric acid crystals by reaction on the neutral substance coating. Then follows a second wetting with the third one-third of the solution; then 12.9% monosodium citrate and, finally, 5.2% sodium carbonate are added. The effervescent grains are dried while mixing them slowly by applying a vacuum, at a temperature of at least 50° C., to 15 mbar. The basic effervescent granular product is screened to 1.5 mm and mixed with 11.0% of ranitidine hydrochloride, 6.5% of mannitol, 6.5% of anti-foaming particles plus 0.2% of flavoring, and pressed to tablets of 1.55 g, which have a disintegration time of 50 sec at a hardness of 7.3 and an acid-neutralizing capacity of less than 2 meq.

EXAMPLE 10

Vehicle crystal grains coated only with a neutral substance:

Since cisapride, for example, in comparison to ranitidine, is not as highly sensitive to acid, it is nevertheless also possible by the procedure to be described below to achieve protection against the acid, all the more so since the drug is embedded in granules.

a) Preparation of the acid crystals coated with a neutral substance:

593 parts by weight of crystalline citric acid plus 70 parts by weight of citric acid powder are heated to 60° C. Then a solution of 4 parts by weight of sorbitol in 4 parts by weight of water is applied and distributed onto the surface of the citric acid by mixing. Finally the citric acid thus coated is vacuum dried at 50 to 60° C.

In the case of both the form of effervescent product presented here and that of effervescent grains which contain a second alkali or alkali earth carbonate coating, it is possible to protect cisapride, for example, against attack by the citric acid in the drug granules by the addition of sodium bicarbonate.

b) Preparation of the drug granules 160 parts by weight of mannitol, 10 parts by weight of cisapride, 5 parts by weight of aerosil and 10 parts by weight of sodium bicarbonate are heated with mixing to 60° C. Then half of a solution of 27 parts by weight of methyl ethyl ketone (or 45 parts by weight of acetone), 2 parts by weight of alcohol, 2 parts by weight of poly(vinyl pyrrolidone) K30, 1 part by weight of propylene glycol and 0.8 parts by weight of docusate sodium are added and distributed for 5 minutes for the purpose of uniform wetting. The mixture is dried to 0.8 bar, the second part of this solution is aspirated, and again distributed by stirring for 5–10 minutes, and finally vacuum dried.

The active agent granules are then screened to 0.3 mm and already have an enhanced protection against acid attack simply due to the sodium bicarbonate they contain. They can then be mixed with the acid crystals coated with neutral substance, the remaining carbonates and bicarbonates, as well as the other tablet ingredients, and pressed to give tablets.

c) Preparation of the final mixture

The citric acid dried and coated according to a) is then mixed with the drug granules prepared according to b), 50 parts by weight of sweetener, 80 parts by weight of sodium carbonate, 430 parts by weight of sodium bicarbonate, and 50 parts by weight of maltodextrin, 100 parts by weight of lactose, 150 parts by weight of mannitol, 50 parts by weight of an antifoaming granulate, and 20 parts by weight of flavoring, and then pressed to tablets of about 1.6 g, which have a disintegration time of 60 to 70 seconds at a hardness of 7.

EXAMPLE 11
Cisapride effervescent tablets a) Preparation of the effervescent granules:

Citric acid, consisting of an amount of 300 parts by weight of granules, 80 parts by weight of fine granules and 40 parts by weight of powder, together with 5 parts by weight of saccharin sodium, is uniformly wet at 60° C. with 2.2 parts by weight of a solution which contains 0.4 part by weight of sorbitol, 0.15 part by weight of sodium bicarbonate, 0.45 part by weight of citric acid and 1.2 parts by weight of water. 12 parts by weight of malic acid are then aspirated in and uniformly anchored on the sorbitol layer formed on the citric acid crystals. Finally, 205 parts by weight of sodium bicarbonate and 1.2 parts by weight of aspartame are aspirated in and once again uniformly distributed. Finally, the material is covered with 46 parts by weight of sodium carbonate, vacuum-dried and discharged through a 1.2 mm sieve.

b) Preparation of the active ingredient granules:

12 parts by weight of polyvinylpyrrolidone are dissolved in 12 parts by weight of ethanol; 6 parts by weight of propylene glycol and 6 parts by weight of docusate sodium are then added and the mixture is diluted with 165 parts by weight of ethyl methyl ketone. Half of this solution is distributed over a mixture of 960 parts by weight of mannitol, 30 parts by weight of Aerosil®, 60 parts by weight of sodium bicarbonate and 61 parts by weight of cisapride, which is heated to 60° C. Partial drying is then carried out in vacuo, and further wetting is effected with the second half of the solution, followed by complete drying and discharge through a 0.3 mm sieve. The final mixture is prepared analogously to Example 5.

EXAMPLE 12
Ranitidine effervescent tablets with 6 wt.% (150 pbw) trisodium citrate The preferred composition contains:

| [wt %] | [pbw] | |
|---|---|---|
| 40 | 1000 | coarse citric acid |
| 10 | 250 | powdered citric acid |
| 0.04 | 1 | trisodium citrate |
| 0.12 | 3 | sorbitol |
| 20 | 500 | sodium bicarbonate |
| 6 | 150 | trisodium citrate, anh. |
| 4 | 100 | sodium carbonate |
| 6.68 | 167 | ranitidine-HCl |
| 5 | 125 | mannitol |
| 4.02 | 100.5 | mannitol/simethicone phase |
| 4.14 | 103.5 | flavor and sweeteners |
| 100% | 2500 pbw | | a) Preparation of the effervescent grains:

40 wt.% (1000 parts by weight; pbw) of coarse crystalline citric acid and 10% (250 pbw) of citric acid powder are heated in a vacuum mixing tank at 60° C. Then a solution consisting of 0.12% (6 pbw) water, 0.04% (1 pbw) trisodium citrate and 0.12% (3 pbw) sorbitol is aspirated in and distributed by stirring. Next, 20% (500 pbw) sodium bicarbonate are added and allowed to react and thereafter 6% (150 pbw) of anhydrous trisodium citrate are added. Finally, 4% (100 pbw) of sodium carbonate are added and the grains are vacuum-dried under slow stirring until a vacuum of 15 mbar is reached.

b) Preparation of the final mixture:

To the effervescent grains thus prepared 6.68% (167 pbw) of ranitidine hydrochloride, 5% (127 pbw) of mannitol plus 4.02% (100.5 pbw) of a granulated antifoaming agent (consisting of 4% mannitol and 0.02% of simethicone) and 4.14% (103.5 pbw) of sweetening and flavoring agents are added. This mixture is mixed for 15 minutes to achieve uniform distribution and then pressed into tablets of 2.5 g.

The tablets have a disintegration time of 60 to 80 seconds and an acid-neutralizing capacity of about 2 meq.

EXAMPLE 13
Ranitidine effervescent tablets with 12 wt.% (300 pbw) of trisodium citrate The preferred composition contains

| [wt. %] | [pbw] | |
|---|---|---|
| 37 | 925 | coarse citric acid |
| 10 | 250 | powdered citric acid |
| 0.04 | 1 | trisodium citrate |
| 0.12 | 3 | sorbitol |
| 14 | 350 | sodium bicarbonate |
| 12 | 300 | trisodium citrate, anh. |
| 4 | 100 | sodium carbonate |
| 6.68 | 167 | ranitidine-HCl |
| 10 | 250 | mannitol: |
| 4.02 | 100.5 | mannitol/simethicone phase |
| 2.14 | 53.5 | sweeteners and flavor |
| 100% | 2500 pbw | |

The preparation of the effervescent grains and of the final mixture is essentially the same as in Example 12. The resulting tablets have a disintegration time of 60 to 80 seconds and an acid-neutralizing capacity of about 2 meq.

EXAMPLE 14
Ranitidine effervescent tablets with tartaric acid instead of citric acid A preferred composition is as follows:

| [%] | [pbw] | |
|---|---|---|
| 35 | 875 | coarse tartaric acid |
| 9 | 225 | powdered tartaric acid |
| 0.22 | 5.5 | sorbitol |
| 30 | 750 | sodium bicarbonate |
| 4 | 100 | sodium carbonate, anh. |
| 6.68 | 167 | ranitidine-HCl |
| 7 | 175 | mannitol |
| 4.02 | 100.5 | mannitol/simethicone phase |
| 4.08 | 102 | orange flavor "PAC" |
| 100% | 2500 pbw | | a) Preparation of the effervescent grains:

35 wt.% of coarse crystalline tartaric acid and 9% tartaric acid powder are heated in a vacuum mixing tank at 60° C. Then a solution consisting of 0.24% water and 0.22% sorbitol is aspirated in and distributed by stirring. Next, 30% sodium bicarbonate are added and allowed to react. Finally, 4% anhydrous sodium carbonate are added and the grains are vacuum dried under slow stirring until a vacuum of 15 mbar is reached.

b) Preparation of the final mixture:

To the effervescent grains thus prepared 6.68% ranitidine hydrochloride, 7mannitol plus 4.02% granulated antifoaming agent (consisting of 4% mannitol and 0.02% simethicone) and 4.08% sweetening and flavoring agents are added. This mixture is mixed for 15 minutes to achieve uniform distribution and then pressed into tablets of 2.5 g.

The tablets have a disintegration time of 60 to 80 seconds and an acid-neutralizing capacity of about 2–3 meq.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An effervescent tablet or granular product suitable for preparing an aqueous solution or suspension of at least one pharmaceutically active substance for oral administration, comprising effervescent grains which contain carrier crystals of at least one solid edible organic acid which are covered by
    i) at least one coating which contains at least one neutral substance able to depress the melting point of the surface of said organic acid crystals and which is soluble in at least one solvent selected from the group consisting of water and alcohol; and
    ii) at least one further coating containing at least one substance selected from the group consisting of alkali carbonate, alkali bicarbonate and alkaline earth carbonate, which has partially reacted with the carrier crystals of at least one solid edible organic acid, wherein
    iii) said at least one further coating optionally further comprises at least one substance selected from the group consisting of an alkali salt of an edible organic acid, an alkaline earth salt of an edible organic acid and at least one of said neutral substance mentioned under i), and
    wherein said tablet or granular product has a disintegration time of less than 180 seconds in water at room temperature, said coating i) separates said at least one solid edible organic acid carrier crystals from said coating ii) but is present in an amount that allows a partial reaction of the coating ii) with the carrier crystals of said at least one solid edible organic acid.

2. The tablet or granular product according to claim 1, wherein said at least one neutral substance is a water-soluble polymer.

3. The tablet or granular product according to claim 1, wherein a moisture-binding agent is anchored on said effervescent grains.

4. The granular effervescent product or tablet according to claim 1, further comprising at least one antifoaming agent.

5. The tablet or granular product according to claim 4, wherein the antifoaming agent is selected from the group consisting of dimethicone and simethicone and is applied in-an amount of from about 0.005 to about 0.5% by weight relative to said tablet or granular product as a whole, corresponding to an amount of about 0.05 to about 2.0% by weight relative to said pharmaceutically active substance(s).

6. The tablet or granular product according to claim 1, having an acid-neutralizing capacity of less than 5 meq, measured according to test 301 of USP XXIII.

7. The tablet or granular product according to claim 1, having a total weight of no more than 2.5 grams and a disintegration time of less than 180 seconds in water at room temperature.

8. The tablet or granular product according to claim 1, comprising at least one hydrophobic pharmaceutically active substance present in particles separate from said effervescent grains, in which particles of said at least one hydrophobic substance is anchored on or coated onto at least one substance selected from the group consisting of a said neutral substance and a suspending agent.

9. The tablet or granular product according to claim 8, wherein the granules further contain at least one component selected from the group consisting of a binder, tenside, alkali carbonate, alkali bicarbonate and alkaline earth carbonate.

10. The tablet or granular product according to claim 1, which comprises, relative to said tablet or granular product as a whole,
    a) about 2 to about 30% by weight of cimetidine;
    b) about 30 to about 60% by weight of said at least one solid edible organic acid;
    c) about 12 to about 40% by weight of said at least one substance listed under ii) and iii);
    d) about 1 to about 4% by weight of at least one sweetener;
    e) about 0.01 to about 30% by weight of said at least one neutral substance;
    f) about 0.005 to about 0.5% by weight of an antifoaming agent; and
    g) about 0.1 to about 3% by weight of a flavoring agent.

11. The tablet or granular product according to claim 1, which comprises, relative to said tablet or granular product as a whole,
    a) about 0.4 to about 4.5% by weight of cisapride;
    b) about 0.4 to about 4.5% by weight of a suspending agent;
    c) about 0.1 to about 1% by weight of a binder component;
    d) about 0.03 to about 0.35% by weight of a tenside component;
    e) about 30 to about 55% by weight of said at least one solid edible organic acid;
    f) about 12 to about 40% by weight of said at least one substance listed under ii) and iii);
    g) about 0.3 to about 2.5% by weight of a sweetener;
    h) about 0.02 to about 55% by weight of said at least one neutral substance;

k) about 0.005 to about 0.05% by weight of antifoaming agent; and l) about 0.2 to about 5% by weight of a flavoring agent.

12. The tablet or granular product according to claim 1, further containing, relative to said tablet or granular product as a whole,
    a) about 0.1 to about 0.5% by weight of betacarotene (100%);
    b) about 2% by weight or less of tocopherol acetate (100%);
    c) about 35 to about 70% by weight of said at least one solid, edible organic acid;
    d) about 11 to about 38% by weight of said at least one substance listed under ii) and iii);
    e) about 1 to about 4% by weight of a sweetener;
    f) about 0.1 to about 35.0% by weight of said at least one neutral substance; and
    g) about 0.3 to about 3% by weight of a flavoring agent.

13. The tablet or granular product according to claim 1, which comprises, relative to said tablet or granular product as a whole,
    a) about 3 to about 14% by weight of ranitidine hydrochloride (75–300 mg per dose);
    b) about 30 to about 55% by weight of said at least one edible organic acid selected from the group consisting of citric acid and tartaric acid;
    c) about 20% by weight or less of monosodium citrate; d) about 10 to about 35% by weight of sodium bicarbonate;
    e) about 2 to about 10% by weight of sodium carbonate;
    f) about 1 to about 3% by weight of at least one sweetener;
    g) about 0.05 to about 15% by weight of said at least one neutral substance;
    h) about 8% by weight or less of antifoaming particles, and
    k) about 0.1 to about 4% by weight of a flavoring agent.

14. An effervescent tablet which comprises:
    a) at least one pharmaceutically active substance and
    b) an effervescent system comprising carrier crystals of at least one solid, edible, organic acid, at least one alkali metal carbonate or bicarbonate as a gas-forming component and at least one alkali metal salt of said at least one organic acid, said carrier crystals being coated by at least two layers wherein the second layer contains at least one alkali metal salt of said at least one organic acid and the first layer contains at least one component selected from the group consisting of another solid edible organic acid and an alkali metal salt thereof and at least one neutral substance which is a water-soluble polymer, wherein said effervescent tablet has a disintegration time of less than 180 seconds in water at room temperature, and said first layer is present in an amount that allows a partial reaction of said carrier crystals with said gas forming component.

15. The tablet or granular product according to claim 1, further comprising cisapride as a said pharmaceutically active substance and having an acid-neutralizing capacity of less than 5 meq at a total weight of less than 2 grams.

16. The tablet or granular product according to claim 1, further comprising cimetidine as a said pharmaceutically active substance and having an acid-neutralizing capacity of less than 5 meq at a total weight of less than 2.5 grams.

17. The tablet or granular product according to claim 1, further comprising ranitidine as a said pharmaceutically active substance and having an acid-neutralizing capacity of less than 3 meq at a total weight of less than 2.6 grams.

18. A method for the preparation of an effervescent tablet or granular product comprising the steps of:
    a) wetting carrier crystals of at least one solid, edible organic acid with a solution of at least one neutral substance,
    b) admixing and uniformly distributing—before complete drying—at least one component in powder form selected from the group consisting of an alkali carbonate, alkali bicarbonate and alkaline earth carbonate, thereby anchoring the same on said wet crystals of a) resulting in a formation of effervescent grains,
    c) drying said effervescent grains and
    d) admixing thereto at least one pharmaceutically active substance and optionally at least one pharmaceutically acceptable adjuvant,
    wherein said method forms an effervescent tablet or granular product that has a disintegration time of less than 180 seconds in water at room temperature, said neutral substance being present in an amount that allows a partial reaction of said at least one component in powder form with said carrier crystals.

19. The method according to claim 18, wherein at least one additional coating is applied onto said effervescent grains obtained by step b) by wetting them with a solution of at least one alkali salt or alkaline-earth salt of a solid edible organic acid.

20. The method according to claim 18, wherein said at least one neutral substance of a) is a water-soluble polymer.

21. The method according to claim 18, further comprising admixing in step d) also a granular antifoaming product which has been prepared by applying a solution of an antifoaming agent onto particles of a said at least one neutral substance and removing the solvent.

22. The method according to claim 18, wherein the drying step c) comprises a sequence of vacuum drying, wetting the dried effervescent grains with ethanol and redrying the grains to remove said ethanol along with residual moisture.

23. The method according to claim 18, wherein said at least one pharmaceutically active substance in step d) is admixed in a form of granules separate from the effervescent grains, which granules are prepared by providing said pharmaceutically active substance together with at least one agent selected from the group consisting of a binding agent and a tenside in a solution and thereafter applying said solution onto particles of at least one suspending agent by uniform distribution yielding coated particles and drying said coated particles thereafter.

24. The method according to claim 18, wherein said at least one pharmaceutically active substance is mixed—prior to being admixed to the effervescent system—with particles of at least one neutral substance, at least one suspending agent and at least one substance selected from the group consisting of alkali carbonate, alkali bicarbonate, alkaline earth carbonate, alkali salt of a solid edible organic acid and alkaline earth salt of a solid edible organic acid, whereafter a solution of at least one agent selected from the group consisting of a binding agent and a tenside is at least once applied to and distributed on said particles of the mixture and the mixture is dried.

25. A process for the manufacture of effervescent granules from a powdered or granular mixture of a solid edible organic acid and at least one compound selected from the group consisting of alkali carbonate, alkali bicarbonate and alkaline earth carbonate, comprising the steps of:
    a) heating said mixture in a tank under vacuum and passivating the surface of at least one of the components of said heated mixture by adding thereto a metered quantity of a polar solvent, said polar solvent further contains dissolved therein at least one neutral substance which is a water-soluble polymer, thereby triggering chemical reactions resulting in liberation of carbon dioxide, b) determining volume and mass of said liberated carbon dioxide by measuring and evaluating pressure differences up to a maximum of 1000 mbar resulting from said liberation of carbon dioxide, c) drying said mixture resulting in step a) and d) repeating steps a) through c) until an evident slowdown of said chemical reactions and a reduced development of carbon dioxide indicate a sufficient degree of passivation, wherein said process forms effervescent granules that have a disintegration time of less than 180 seconds in water at room temperature.

26. A process for the preparation of an effervescent granular material containing at least one solid edible organic acid and at least one carbonate of an alkali metal or an alkaline earth metal which splits off $CO_2$ upon reaction with said organic acid in aqueous solution, the process comprising the steps of:

a) pre-reacting a portion of said at least one edible organic acid and of said at least one carbonate in at least one solvent selected from the group consisting of water and alcohol to form a solution of pre-reaction product, wherein the solution of said pre-reaction product further contains at least one neutral substance selected from the group consisting of a polymer soluble in water and a polymer soluble in alcohol, b) applying said pre-reaction product onto crystals of another portion of said at least one edible organic acid under thorough mixing to form a first coating by reaction with said crystals and liberation of resulting water of crystallization, c) applying at least one additional coating onto said organic acid crystals with said first coating, said additional coating comprising another portion of said at least one carbonate, and d) terminating the process by drying after the last coating has been applied, wherein said process forms effervescent granules that have a disintegration time of less than 180 seconds in water at room temperature.

27. The tablet or granular product according to claim 1, wherein said at least one neutral substance is present in said at least one coating under i) in an amount of from about 0.05 to about 1.0% by weight relative to said tablet or granular product as a whole.

28. The tablet or granular product according to claim 3, wherein said moisture-binding agent is selected from the group consisting of anhydrous sodium carbonate and sodium sulfate and is applied in an amount of from about 4 to about 10% by weight relative to said tablet or granular product as a whole.

29. The tablet or granular product according to claim 4, wherein said at least one antifoaming agent is present in at least one of said further coatings under ii).

30. The tablet or granular product according to claim 4, wherein said antifoaming agent is present in particles separate from the effervescent grains.

31. The tablet or granular product according to claim 6, wherein the acid neutralizing capacity is less than 3 meq.

32. The tablet or granular product according to claim 7, wherein said total weight is no more than 2.0 grams and the disintegration time is less than 120 seconds.

33. The tablet or granular product according to claim 8, wherein said at least one suspending agent is selected from the group consisting of Aerosil® and Avicel® and said neutral substance is selected from the group consisting of mannitol and sorbitol.

34. The tablet or granular product according to claim 9, wherein the binder is polyvinylpyrrolidone (PVP) and the tenside is dioctyl sodium sulfosuccinate or sodium lauryl sulfate.

35. The tablet or granular product according to claim 10, wherein said at least one component under c) comprises, relative to said tablet or granular product as a whole, about 2 to about 10% by weight of sodium carbonate as a moisture binding agent and wherein a portion of said at least one neutral substance under e) amounting to about 0.01 to about 0.05% by weight relative to said tablet or granular product as a whole is located in said at least one coating of said carrier crystals.

36. The tablet or granular product according to claim 10, wherein said at least one neutral substance under e) comprises, relative to said tablet or granular product as a whole, about 3 to about 20% by weight of sorbitol and about 2 to about 10% by weight of mannitol.

37. The tablet or granular product according to claim 11, wherein said binder under c) is polyvinylpyrrolidone (PVP), said tenside under d) is dioctyl sodium sulfosuccinate, said edible organic acid under e) is citric acid, said at least one component under f) comprises, relative to said tablet or granular product as a whole, about 2 to about 10% by weight of sodium carbonate as a moisture-binding agent, said at least one neutral substance under h) comprises, relative to said tablet or granular product as a whole, a portion of about 0.02 to about 0.1% by weight that is located in said at least one coating of said carrier crystals, and said-antifoaming agent under i) is selected from the group consisting of dimethicone and simethicone.

38. The tablet or granular product according to claim 11, wherein said at least one neutral substance under h) is selected from the group consisting of sorbitol, maltodextrin, lactose and mannitol.

39. The tablet or granular product according to claim 12, wherein said at least one edible organic acid under e) comprises, relative to said tablet or granular product as a whole, about 10% by weight or less of ascorbic acid, about 35 to about 55% by weight of citric acid and about 5% by weight or less of malic acid, said at least one component under d) comprises about 5 to about 15% by weight of calcium carbonate and about 5 to about 20% by weight of sodium bicarbonate and said at least one neutral substance under f) comprises a portion of about 0.1 to about 0.5% by weight, relative to said tablet or granular product as a whole, that is located in said at least one coating of said carrier crystals.

40. The tablet or granular product according to claim 12, wherein said at least one neutral substance under f) comprises, relative to said tablet or granular product as a whole, about 1 to about 10% by weight of sorbitol and about 5 to about 25% by weight of mannitol.

41. The tablet or granular product according to claim 15, wherein said acid neutralizing capacity is less than 3 meq at a total weight of less than about 1.6 grams.

42. The tablet or granular product according to claim 16, wherein said acid neutralizing capacity is less than 3 meq at a total weight of less than about 2.0 grams.

43. The tablet or granular product according to claim 17, wherein said acid neutralizing capacity is less than 2 meq at a total weight of less than 2.0 g.

44. The method according to claim 18, for the preparation of an effervescent tablet further comprising a step of compressing said effervescent grains together with said pharmaceutically active substance and said at least one optional adjuvant into tablets.

45. The method according to claim 18, wherein said pharmaceutically active substance is acid-sensitive.

46. The method according to claim 18, wherein said pharmaceutically active substance is acid-sensitive and selected from the group consisting of H2-blockers, cisapride and beta-carotene.

47. The method according to claim 45, wherein said H2-blocker is selected from the group consisting of cimetidine and ranitidine.

48. The method according to claim 22, further comprising an antifoaming agent dissolved in said ethanol.

49. The tablet or granular or product according to claim 1, wherein said at least one neutral substance is a polyalcohol.

50. The tablet or granular or product according to claim 14, wherein said at least one neutral substance is a polyalcohol.

51. The tablet or granular or product according to claim 20, wherein said at least one neutral substance is a polyalcohol.

52. The tablet or granular or product according to claim 25, wherein said at least one neutral substance is a polyalcohol.

53. The tablet or granular or product according to claim 26, wherein said at least one neutral substance is a polyalcohol.

54. The tablet or granular product according to claim 1, wherein said tablet or granular product is a tablet.

55. The tablet or granular product according to claim 1, wherein said tablet or granular product is a granular product.

56. The method according to claim 18, wherein said method forms an effervescent tablet.

57. The method according to claim 18, wherein said method forms a granular product.

58. The tablet or granular product according to claim 1, wherein said tablet or granular product further comprises an acid sensitive drug.

59. An effervescent tablet or granular product suitable for preparing an aqueous solution or suspension of at least one acid sensitive pharmaceutically active substance for oral administration, comprising (i) an acid sensitive pharmaceutically active substance and (ii) effervescent grains which contain carrier crystals of at least one solid edible organic acid which are covered by p1 i) at least one coating which contains at least one neutral substance able to depress the melting point of the surface of said organic acid crystals and which is soluble in at least one solvent selected from the group consisting of water and alcohol; and ii) at least one further coating containing at least one substance selected from the group consisting of alkali carbonate, alkali bicarbonate and alkaline earth carbonate which has partially reacted with the carrier crystals of at least one solid edible organic acid, wherein iii) said at least one further coating optionally further comprises at least one substance selected from the group consisting of an alkali salt of an edible organic acid, an alkaline earth salt of an edible organic acid and at least one of a said neutral substance mentioned under i), wherein said tablet or granular product has a disintegration time of less than 180 seconds in water at room temperature, said coatings i) and ii) and optionally iii) separate said acid sensitive pharmaceutically active substance from said carrier crystals of at least one solid edible organic acid, the coating i) separates the at least one solid edible organic acid carrier crystals from said coating ii), and said coating i) is present in an amount that allows a partial reaction of coating ii) with the carrier crystals of said at least one solid edible organic acid.

60. The tablet or granular product according to claim 1, wherein said at least one neutral substance is a carbohydrate.

61. The tablet or granular product according to claim 1, wherein said at least one neutral substance is a hydrocolloid.

62. The tablet or granular product according to claim 14, wherein said at least one neutral substance is a carbohydrate.

63. The tablet or granular product according to claim 14, wherein said at least one neutral substance is a hydrocolloid.

64. The tablet or granular product according to claim 20, wherein said at least one neutral substance is a carbohydrate.

65. The tablet or granular product according to claim 20, wherein said at least one neutral substance is a hydrocolloid.

66. The tablet or granular product according to claim 25, wherein said at least one neutral substance is a carbohydrate.

67. The tablet or granular product according to claim 25, wherein said at least one neutral substance is a hydrocolloid.

68. The tablet or granular product according to claim 26, wherein said at least one neutral substance is a carbohydrate.

69. The tablet or granular product according to claim 26, wherein said at least one neutral substance is a hydrocolloid.

70. The tablet or granular product according to claim 1, wherein said at least one neutral substance is selected from the group consisting of polyvinylpyrrolidone, polyethyleneglycol, carbopol, polyvinyl alcohol, polyvinyl acetate, saccharose, pentaerythritol, glucose, fructose, maltodextrin, dextrin, xanthan, guargum, tragacanth, galactomanan, petkine, xylitol, mannitol, sorbitol, dextrose, maltose, cellobioze, lactose, saccharose, starch, cellulose and petkin.

71. The tablet or granular product according to claim 59, wherein said neutral substance is present in an amount of 0.05–1% by weight relative to said tablet or granular product as a whole.

* * * * *

UNITED STATES PATENT AND TRADEMARK OFFICE
CERTIFICATE OF CORRECTION

PATENT NO. : 5,792,473
DATED : August 11, 1998
INVENTOR(S) : Gergely et al.

It is certified that error appears in the above-identified patent and that said Letters Patent is hereby corrected as shown below:

ON THE TITLE PAGE:
Inventors name should read --

Gerhard Gergely--.

Please insert the Related U.S. Application Data under section [63] as follows:

--Continuation-in-Part of PCT/EP95/00650, filed February 23, 1995--.

Please insert the Foreign Application Priority Data under section [30] as follows:

--March 1, 1994 [DE] P4406641.4
March 23, 1994 [CH] 873/94-6
October 26, 1994 [EP] 94203112.1--.

UNITED STATES PATENT AND TRADEMARK OFFICE
CERTIFICATE OF CORRECTION

PATENT NO. : 5,792,473
DATED : August 11, 1998
INVENTOR(S) : Gergely et al.

It is certified that error appears in the above-identified patent and that said Letters Patent is hereby corrected as shown below:

Claim 11 (column 17, line 1) please re-letter section "k)" as --i)--.

Claim 11 (column 17, line 3) please re-letter section "l)" as --j)--.

Claim 12 (column 17, line 5) please change "further containing" to --which comprises--.

Claim 13, (column 17, line 38) please re-letter section "k)" as --i)--

UNITED STATES PATENT AND TRADEMARK OFFICE
CERTIFICATE OF CORRECTION

PATENT NO. : 5,792,473
DATED : August 11, 1998
INVENTOR(S) : Gergely et al.

It is certified that error appears in the above-identified patent and that said Letters Patent is hereby corrected as shown below:

Claim 49 (column 21, line 10), please delete "or" (second occurrence).

Claim 50 (column 21, line 12), please delete "or" (second occurrence).

Claim 51 (column 21, line 15), please delete "or" (second occurrence).

Claim 52 (column 21, line 18), please delete "or" (second occurrence).

Claim 53 (column 21, line 21), please delete "or" (second occurrence).

Signed and Sealed this

Eighteenth Day of April, 2000

Attest:

Q. TODD DICKINSON

*Attesting Officer*  *Director of Patents and Trademarks*